(12) United States Patent
Zur et al.

(10) Patent No.: US 12,383,730 B2
(45) Date of Patent: Aug. 12, 2025

(54) ALTERNATING CHARGE TO INHIBIT SORPTION TO SURFACES EXPOSED TO BIOLOGICAL MATERIALS

(71) Applicants: RAMBAM MEDTECH LTD, Haifa (IL); Boaz Zur, Kibbutz Farod (IL); Yehuda Bachar, Yehud-Monosson (IL)

(72) Inventors: Boaz Zur, Kibbutz Farod (IL); Yehuda Bachar, Yehud-Monosson (IL); Gil Zur, Kibbutz Farod (IL)

( * ) Notice: Subject to any disclaimer, the term of this patent is extended or adjusted under 35 U.S.C. 154(b) by 551 days.

(21) Appl. No.: 17/434,749

(22) PCT Filed: Mar. 16, 2020

(86) PCT No.: PCT/IL2020/050312
§ 371 (c)(1),
(2) Date: Aug. 29, 2021

(87) PCT Pub. No.: WO2020/188559
PCT Pub. Date: Sep. 24, 2020

(65) Prior Publication Data
US 2022/0126087 A1    Apr. 28, 2022

Related U.S. Application Data

(60) Provisional application No. 62/819,693, filed on Mar. 18, 2019.

(51) Int. Cl.
| | | |
|---|---|---|
| *A61N 1/05* | (2006.01) | |
| *A61N 1/08* | (2006.01) | |
| *A61N 1/36* | (2006.01) | |
| *A61N 1/20* | (2006.01) | |
| *A61N 1/32* | (2006.01) | |

(52) U.S. Cl.
CPC ............... *A61N 1/05* (2013.01); *A61N 1/08* (2013.01); *A61N 1/36189* (2013.01); *A61N 1/205* (2013.01); *A61N 1/32* (2013.01)

(58) Field of Classification Search
CPC ........ A61N 1/05; A61N 1/08; A61N 1/36189; A61N 1/205; A61N 1/32
See application file for complete search history.

(56) References Cited

U.S. PATENT DOCUMENTS

| | | | | |
|---|---|---|---|---|
| 5,078,736 A | * | 1/1992 | Behl | ............ A61F 2/88 606/41 |
| 5,154,165 A |   | 10/1992 | Elliott et al. | |
| 5,260,020 A | * | 11/1993 | Wilk | ............ A61M 25/0017 606/29 |
| 6,110,423 A | * | 8/2000 | Bushnell | ............ A61L 2/02 422/23 |

(Continued)

*Primary Examiner* — Pamela M. Bays

(57) ABSTRACT

A system and/or method are disclosed to inhibit sorption to a surface in a biological medium and/or biofouling by means of an alternating electric field. For example, one or more insulated electrodes may be positioned near the surface. For example, insulation may limit electric current flow between the biological medium and the electrode and/or between the surface and the electrode and/or between the electrodes. In some embodiments, the alternating charge in the vicinity of the surface may inhibit the buildup of biological films and/or sorption to the surface. For example, the system may be used to inhibit fouling of an implanted medical device (e.g. a catheter).

9 Claims, 13 Drawing Sheets

(56) References Cited

U.S. PATENT DOCUMENTS

| | | | |
|---|---|---|---|
| 6,939,345 B2 | 9/2005 | KenKnight et al. | |
| 7,150,814 B1 | 12/2006 | Parce et al. | |
| 8,951,241 B2 | 2/2015 | Eberli et al. | |
| 9,421,285 B2 | 8/2016 | Fuller et al. | |
| 2001/0001314 A1* | 5/2001 | Davison | A61B 18/1206 606/41 |
| 2005/0288730 A1* | 12/2005 | Deem | A61B 18/1206 607/42 |
| 2009/0131994 A1* | 5/2009 | Rey | A61N 1/327 435/173.6 |
| 2012/0150171 A1 | 6/2012 | Asirvatham et al. | |
| 2016/0193388 A1* | 7/2016 | Joseph | A61L 29/02 604/21 |
| 2017/0056536 A1* | 3/2017 | Hallab | A61F 2/482 |
| 2018/0000599 A1* | 1/2018 | Bermudez Castel | A61N 1/205 |

\* cited by examiner

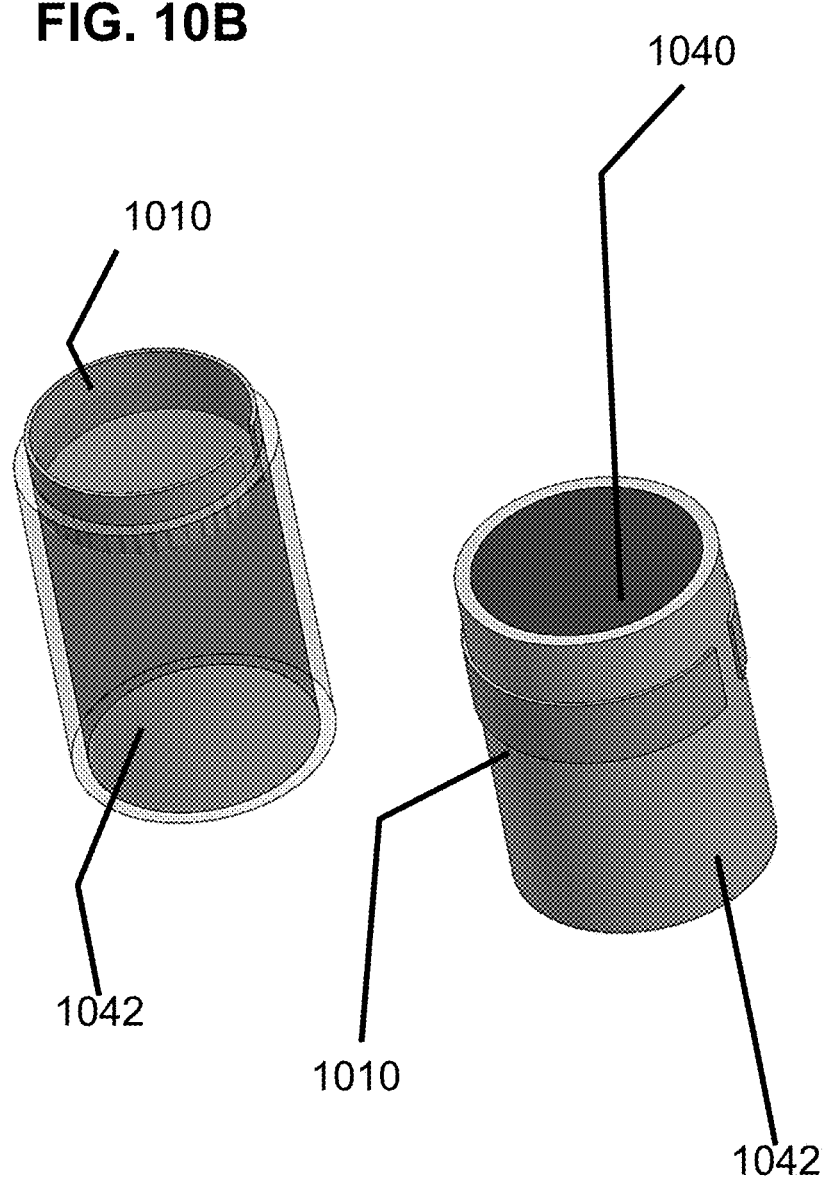

ALTERNATING CHARGE TO INHIBIT SORPTION TO SURFACES EXPOSED TO BIOLOGICAL MATERIALS

RELATED APPLICATION

This application claims the benefit of priority under 35 USC § 119(e) of U.S. Provisional Patent Application No. 62/819,693 filed Mar. 18, 2019, the contents of which are incorporated herein by reference in their entirety.

FIELD AND BACKGROUND OF THE INVENTION

The present invention, in some embodiments thereof, relates to a method and system for inhibiting sorption to a surface and/or biofouling and more particularly but not exclusively to preventing disruption of implanted medical devices by biological sorption and/or fouling processes.

U.S. Pat. No. 8,951,241 appears to disclose, "A medical device," . . . , "which comprises a functional unit (C) for permanent or temporary placement in the urogenital tract of a human or animal body. The functional unit has at least one electrically conducting portion. A power source (G) supplies a current to the electrically conducting portion after placement of the functional unit in the urogenital tract. In this manner, the growth of bacteria on the functional unit can be reduced."

International Patent Application Publication no. WO2012007332(A1) entitled Device and Method for Reducing the Risk of Occlusion and Restenosis after Implantation of a Stent appears to disclose, "A medical device for the permanent or temporal support of the wall of a blood vessel," . . . . "The device comprises an implantable tubular stent (3) having at least one electrically conducting portion, and a power source (2, 4, 5, 6) operable to supply a voltage or current to the electrically conducting portion after implantation of the stent into a blood vessel of a human or animal body. In this manner, the risk of occlusion, stenosis or restenosis of the blood vessel can be reduced. In preferred embodiments, a small surface current density into the surrounding body material in the range of 10-10,000 nA/mm2 is generated. Means for supplying energy to the stent both transcutaneously and through a wall of the blood vessel are also disclosed.

Background art includes US Patent Application Publication no. 2012150171(A1)—Controlling Coagulum Formation; US Patent Application Publication no. 2008281250 (A1) entitled Self-Clearing Catheter for Clinical Implantation; US Patent Application Publication no. 2012197063(A1) entitled Systems and Methods Which Remove Material From Blood Vessel Walls; Soojin Shim, Seok Hoon Hong, Yongsug Tak & Jeyong Yoon (2011) Prevention of *Pseudomonas aeruginosa* adhesion by electric currents, Biofouling, 27:2, 217-224, DOI: 10.1080/ 08927014.2011.554831; U.S. Pat. No. 7,150,814(B1) entitled Prevention of surface adsorption in microchannels by application of electric current during pressure-induced flow; U.S. Pat. No. 6,939,345(B2) entitled Method for reducing restenosis in the presence of an intravascular stent; U.S. Pat. No. 5,154,165(A) entitled Medical devices; US Patent no. 2014309579(A1) entitled Balloon Catheter Method for Reducing Restenosis Via Irreversible Electroporation.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

SUMMARY OF THE INVENTION

According to an aspect of some embodiments of the invention, there is provided an implantable device including: a surface configured to be in contact with at least one body component in vivo; a first electrode positioned close to the surface; an electrical insulator inhibiting current flow between the body component and the first electrode; a power source; a modulator connecting the power source to the first electrode thereby modulating a charge of the first electrode.

According to some embodiments of the invention, a shortest path between the first electrode and the surface is within an internal portion of the implantable device sealed away from the body component and sealed away from the surface.

According to some embodiments of the invention, a shortest path between the first electrode and the surface is not in fluid communication with the body component and not in fluid communication with surface.

According to some embodiments of the invention, the implantable device further includes: a second electrode connected to the modulator for carrying a charge opposite to the first electrode and wherein the second electrode electrically insulated from the surface and electrically insulated from the body component.

According to some embodiments of the invention, the implantable device further includes: a second electrode connected to the modulator for carrying an opposite charge to the first electrode and wherein the second electrode is far away from the first electrode.

According to some embodiments of the invention, the modulator and the power source are configured to produce a current of less than 0.01 Amp.

According to some embodiments of the invention, the surface is electrically non-conductive.

According to some embodiments of the invention, the surface is electrically conductive.

According to an aspect of some embodiments of the invention, there is provided a method of inhibiting sorption to a surface including: providing a charge source electrically insulated from the surface; modulating a charge on the charge source;

retaining the charge source close to the surface.

According to some embodiments of the invention, the retaining includes retaining the charge source in a geometry wherein a shortest path between the charge source is sealed from fluid communication with the surface.

According to some embodiments of the invention, the modulating is at a rate of between 50 to 1000 Hz.

According to some embodiments of the invention, the method further includes: placing the surface in contact with live tissue in vivo and wherein the charge source is insulated from the live tissue.

According to some embodiments of the invention, the method further includes placing the surface in contact with a body fluid in vitro and wherein the charge source is insulated from the body fluid.

According to an aspect of some embodiments of the invention, there is provided a catheter assembly including: a distal portion configured for insertion into a living subject; a lumen in the distal portion; an electrode in the distal portion near the lumen and electrically insulated from the lumen; a power source; a charge modulator in electrical communication between the electrode and the power source for producing an alternating charge on the electrode.

According to some embodiments of the invention, the power source, modulator and electrode are configured to produce the alternating charge of frequency between 50 Hz to 1 kHz a wall of the lumen.

According to some embodiments of the invention, the electrode is retained within 5 mm of the lumen.

According to some embodiments of the invention, the electrode is retained within a wall of the lumen.

According to some embodiments of the invention, the electrode is sealed from fluid communication with an inside of the lumen.

According to some embodiments of the invention, the catheter assembly further includes: a second electrode connected to the modulator for carrying a charge opposite to the alternating charge on the electrode and wherein the second electrode is electrically insulated from the lumen.

According to an aspect of some embodiments of the invention, there is provided a device for inhibiting sorption to a surface including: a first electrode positioned close to the surface; an electrical insulator inhibiting current flow between the surface and the first electrode; a power source; a modulator connecting the power source to the first electrode thereby modulating a charge of the first electrode.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 10A illustrates a piezoelectric device on the outside of an artery in accordance with an embodiment of the current invention FIG. 10B illustrate a piezoelectric device on the inside of an artery in accordance with an embodiment of the current invention;

DESCRIPTION OF SPECIFIC EMBODIMENTS OF THE INVENTION

Figure 1:
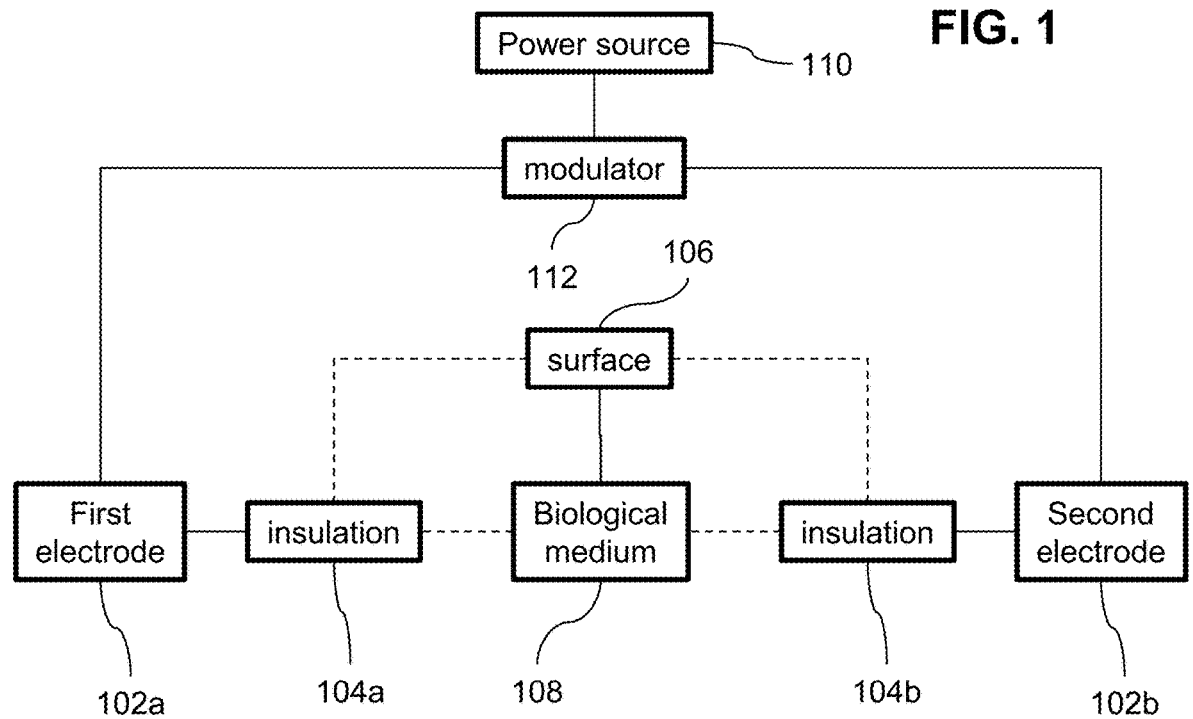
FIG. 1 is a block diagram of a system to inhibit sorption and/or biofouling in a system in accordance with an embodiment of the current invention.

The present invention, in some embodiments thereof, relates to a method and system for inhibiting sorption to a surface and more particularly but not exclusively to preventing disruption of implanted medical devices by biological sorption and/or fouling processes.

Overview

An aspect of some embodiments of the current invention relates to a system and/or method to inhibit sorption to a surface in a biological medium and/or biofouling by means of an alternating electric field. For example, one or more insulated electrodes may be positioned near the surface. For example, insulation around the electrode may prevent electric current from flowing between the biological medium and the electrode. For example, insulation around the electrode may prevent electric current from flowing between the surface and the electrode. For example, insulation around the electrodes may prevent electric current from flowing between the electrodes. In some embodiments, the alternating charge in the vicinity of the surface may inhibit the buildup of biological films and/or sorption to the surface.

An aspect of some embodiments of the current invention relates to a method and/or system to prevent fouling of an implanted medical device (e.g. a catheter). In some embodiments, the system may include one or more electrodes that are positioned near a surface of the device that is in contact with a biological medium, body fluids and/or tissue. Optionally, the electrodes are insulated from the body and/or the surface. Optionally a power source and/or a modulator are used to create an alternating electric field near the surface thereby inhibiting sorption. Optionally the power source may include an implanted battery and modulator and/or an external battery and modulator and/or a piezoelectric device.

SPECIFIC EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a block diagram of a system to inhibit sorption and/or biofouling in a system in accordance with an embodiment of the current invention. In some embodiments one or more electrodes 102a, 102b insulated by insulators 104a, 104b and/or positioned near a surface 106 which is in contact with a biological medium 108. Optionally, the electrodes are charged alternately with positive and/or negative charge. For example, the electrodes may be connected to a power source 110 and a modulator 112. Since the electrodes 102a, 102b are insulated from each other and/or from the medium 108 there may be little or no current between the electrodes 102a, 102b and/or in the medium 108.

In some embodiments a surface 106 may include a face of an object into which the electrode 102a, 102b is embedded. For example, an electrodes 102a, 102b may be embedded into a wall of a catheter. Optionally, the electrodes 102a, 102b may inhibit sorption to an inner and/or outer surface of the catheter. In some embodiments, a first electrode 102a may be within 0.5 mm of the surface and/or between 0.5 to 1 mm from the surface and/or between 1 to 2 mm from the surface and/or between 2 to 5 mm from the surface and/or between 5 to 20 mm from the surface and/or between 20 to 100 mm from the surface 106. Alternatively or additionally, the system may include a second electrode 102b. Optionally, the shortest path between the second electrode 102b and the surface 106 may be through the device without passing through the biological medium 108. For example, electrodes 102a, 102b may be of opposing polarities. For example, the second electrode 102b may be within 0.5 mm of the surface and/or between 0.5 to 1 mm from the surface and/or between 1 to 2 mm from the surface and/or between 2 to 5 mm from the surface and/or between 5 to 20 mm from the surface and/or between 20 to 100 mm from the surface and/or further. Alternatively or additionally, the second electrode 102b may be in electrical contact with the medium 108 and/or the surface 106. In some embodiments, the insulation may interrupt between electrodes 102a and 102b so that there is no path of conduction between the two electrodes 102a and 102b. Alternatively or additionally, the insulation may interrupt between the medium 108 and one or both of electrodes 102a and/or 102b. Alternatively or additionally, the insulation may interrupt between the surface 106 and one or both of electrodes 102a and/or 102b. Optionally, a single piece of insulating material insulates between the electrodes 102a and/or 102b and/or one or both of the electrodes and/or the medium 108 and/or the surface 106. In some embodiments, one of the electrodes 102a, 102b may be in electrical contact with the medium 108 and/or the surface 106.

In some embodiments, a power source 110 and/or the modulator may 112 include a battery and/or a generator and/or a piezoelectric device and/or printed circuit board PCB. Optionally, the power source 110 and/or modulator 112 may be implanted into a subject and/or may be external to the subject.

In some embodiments, the surface 106 being protected may include a surface of an implanted device and/or a catheter. Alternatively or additionally, the surface 106 may be external to a person. For example, the surface may be a part of a laboratory device in contact with a biological medium 108 and/or a pipe and/or a pump vulnerable to growth of biofilms.

Figure 2:
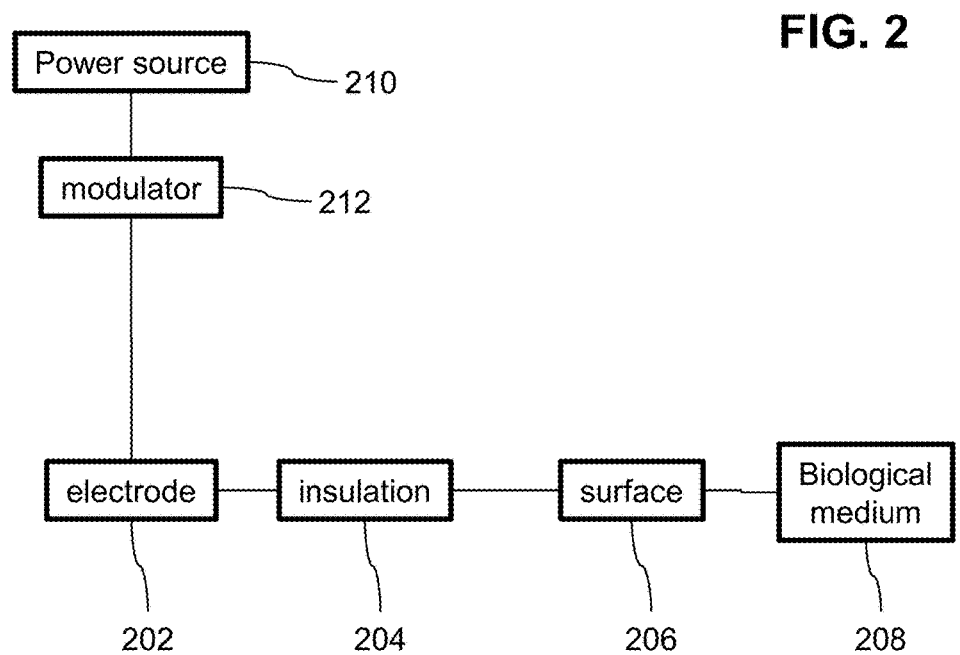
FIG. 2 is a block diagram of a system with a single electrode in accordance with an embodiment of the current invention.

FIG. 2 is a block diagram of a system with a single electrode 202 in accordance with an embodiment of the current invention. Optionally the system of FIG. 1 may have a single electrode 202 (e.g. an alternating electric charge source [e.g. including a power source 210 and/or an oscillator 212]). Optionally the electrode 202 is located near a surface 206 in contact with a biological medium 208. For example, the electrode 202 may produce an alternating electrical field that protects the surface 206 from biofilms and/or other sources of fouling. Additionally or alternatively, the electrode 202 is insulated from the surface 206 being protected and/or the biological medium 208 by an insulator 204.

Figure 3:
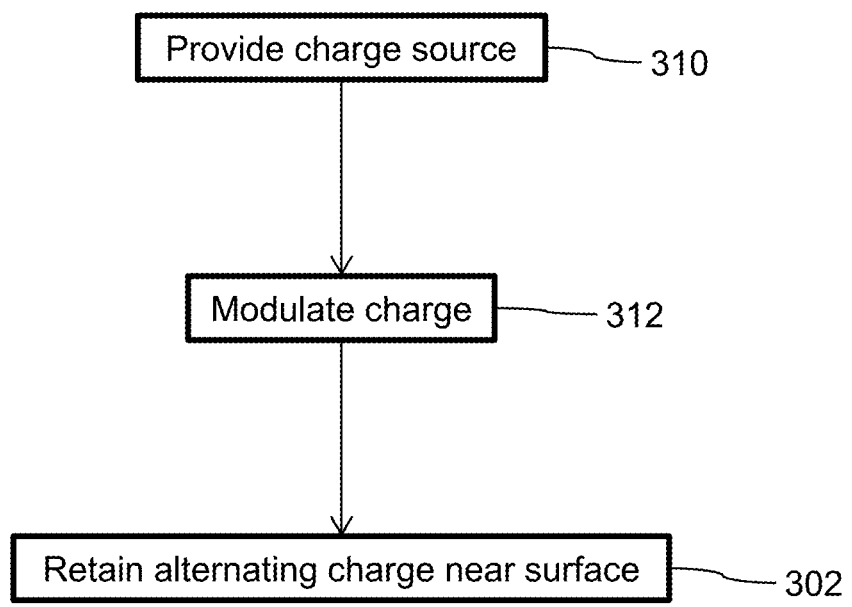
FIG. 3 is a flow chart illustration of a method of inhibiting sorption to a surface in accordance with an embodiment of the current invention.

FIG. 3 is a flow chart illustration of a method of inhibiting sorption to a surface in accordance with an embodiment of the current invention. For example, the method may be used in combination with a system in accordance with FIG. 1 and/or FIG. 2. In some embodiments, a charge source will be provided 310. Optionally, the charge will be modulated 312 to produce a modulated charge. For example, the charge may be alternated 312 at a frequency of between 100 to 500 Hz and/or between 10 to 100 Hz and/or between 1 to 10 Hz and/or between 500 Hz to 4 kHz and/or between 4 kHz to 20 kHz and/or between 20 kHz to 500 kHz. Optionally the strength of the charge may range between ±0.5 to ±2V and/or between ±0.1 to ±0.5V and/or between ±2 to ±5V and/or between ±0.01 to ±0.1V and/or between ±5 to ±20V and/or between ±0.01 to ±0.1V. Optionally the oscillations in charge may have the form of a square wave and/or a sine wave and/or a complex shape and/or a random shape. In some embodiments, the charge will be retained 302 near a surface, for example the charge may be conducted to an electrode near the surface. In some embodiments, a surface in contact with a biological medium may be exposed to an alternating field. Optionally, the field may prevent sorption to the surface and/or protect the surface from biofilms. For example, the surface may include a surface of an implanted medical device and/or a tube through which biological fluids pass and/or a surface exposed to biological fluids. Optionally, there may be little or no current flowing. For example, the charge source may be insulated from the surface and/or the biological fluid.

Figure 4:
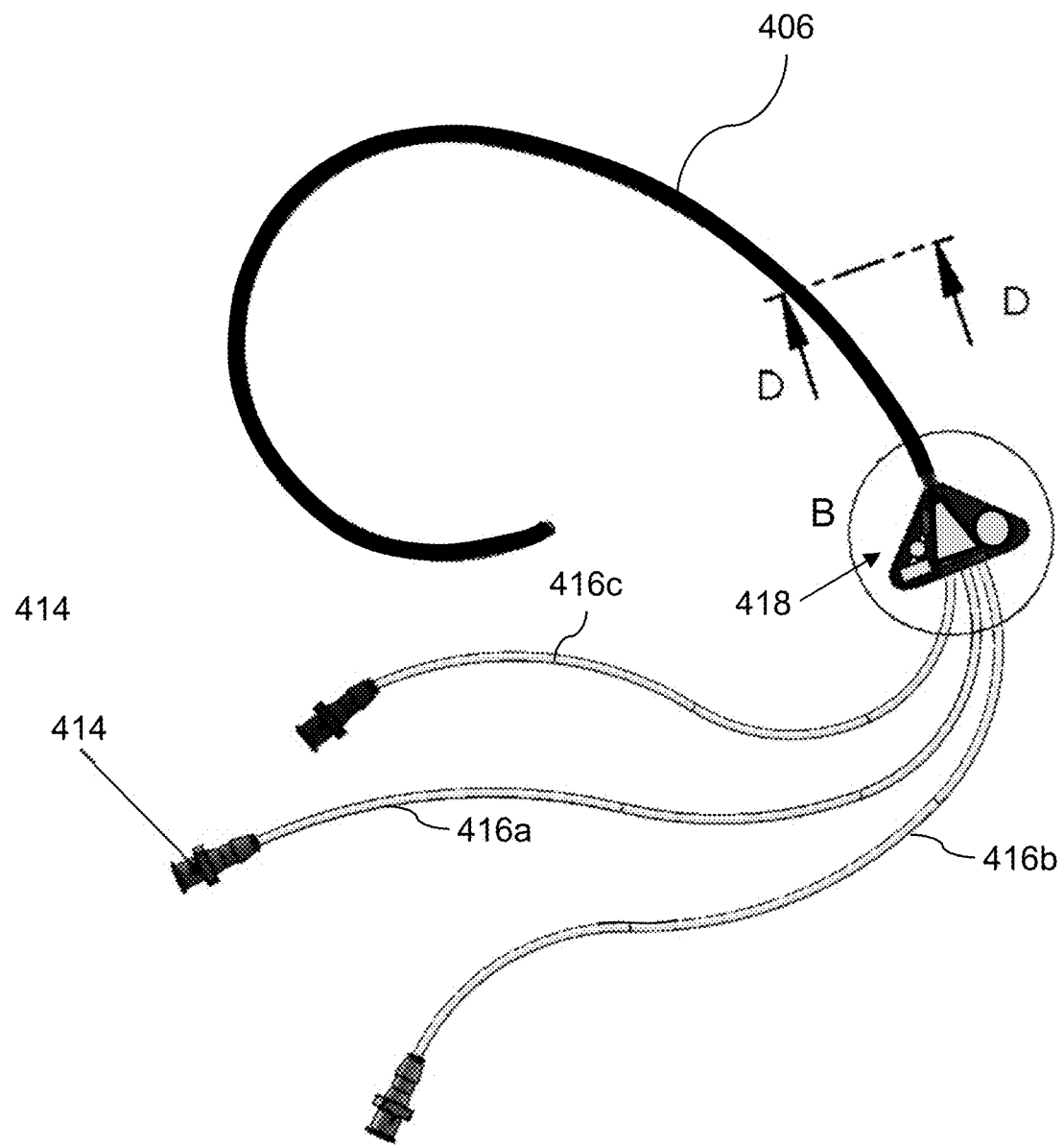
FIG. 4 is a perspective view of a medical tube (e.g. a catheter) in accordance with an embodiment of the current invention.

FIG. 4 is a perspective view of a medical tube 406 (e.g. a catheter) in accordance with an embodiment of the current invention. In some embodiments, a sorption inhibiting system is included in the catheter, for example to prevent fouling of the tube 406. For example, wires and/or electrodes may run along the tube 406. Optionally, the electrodes are insulated within the walls of tube 406 and/or do not contact the fluid on the inside of the tube 406 and/or outside the tube 406. In some embodiments the electrodes may reach and/or be shaped to prevent sorption at the distal end of the tube 406.

Optionally, tube 406 include multiple lumens connected through a hub and/or a bushing 418 (e.g. including a suture wing and/or dividing lumens to separate ports 414). For example, the sorption inhibiting system may include elements built into bushing 418, for example as illustrated in the expanded views of region B, e.g. FIGS. 5A and/or 5B.

In some embodiments, a surface being protected from sorption (e.g. a surface of medical tube 406) may be made of polymeric materials such as Silicone, Polyurethane (PUR), Vinyl, latex, silicone-elastomer coated latex and/or hydrophilic polymer coated latex, rubber and/or polytetrafluoroethylene PTFE (Teflon) coated latex and/or more. Optionally the surface may be coated or not with materials such as silver-alloy coated (anti-microbial) and/or anti-biotic and/or antiseptic and/or others. Optionally, tube 406 may have an outer diameter ranging between 3f to 23f. The medical tube may include 1 to 3 or more lumens for transport of material between outside the tube to a body lumen.

Various types of medical "tubes", including catheters, urinary catheters, and/or stents may be inserted into a patient, for example for providing drugs and/or channeling body fluids (e.g. blood, urine etc.). These devices often have their life span shortened by blockage after a certain period of time. Blockage may a result from activation of the clotting system in the body. In some embodiments, a system in accordance with the current invention may be used to inhibit this blockage.

Figure 5A:
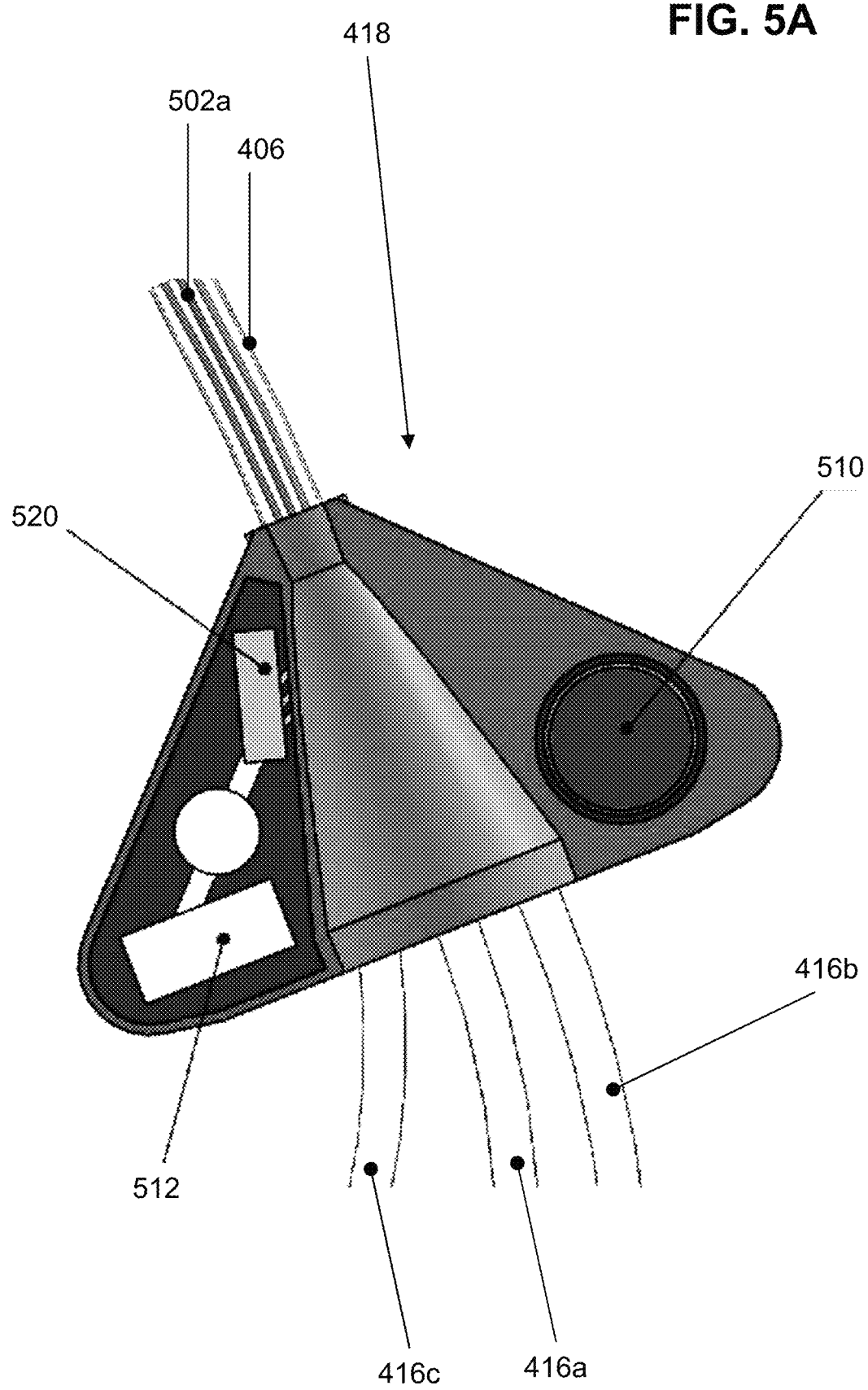
FIG. 5A is a close-up perspective view of a system to prevent sorption in accordance with an embodiment of the current invention.
Figure 5B:
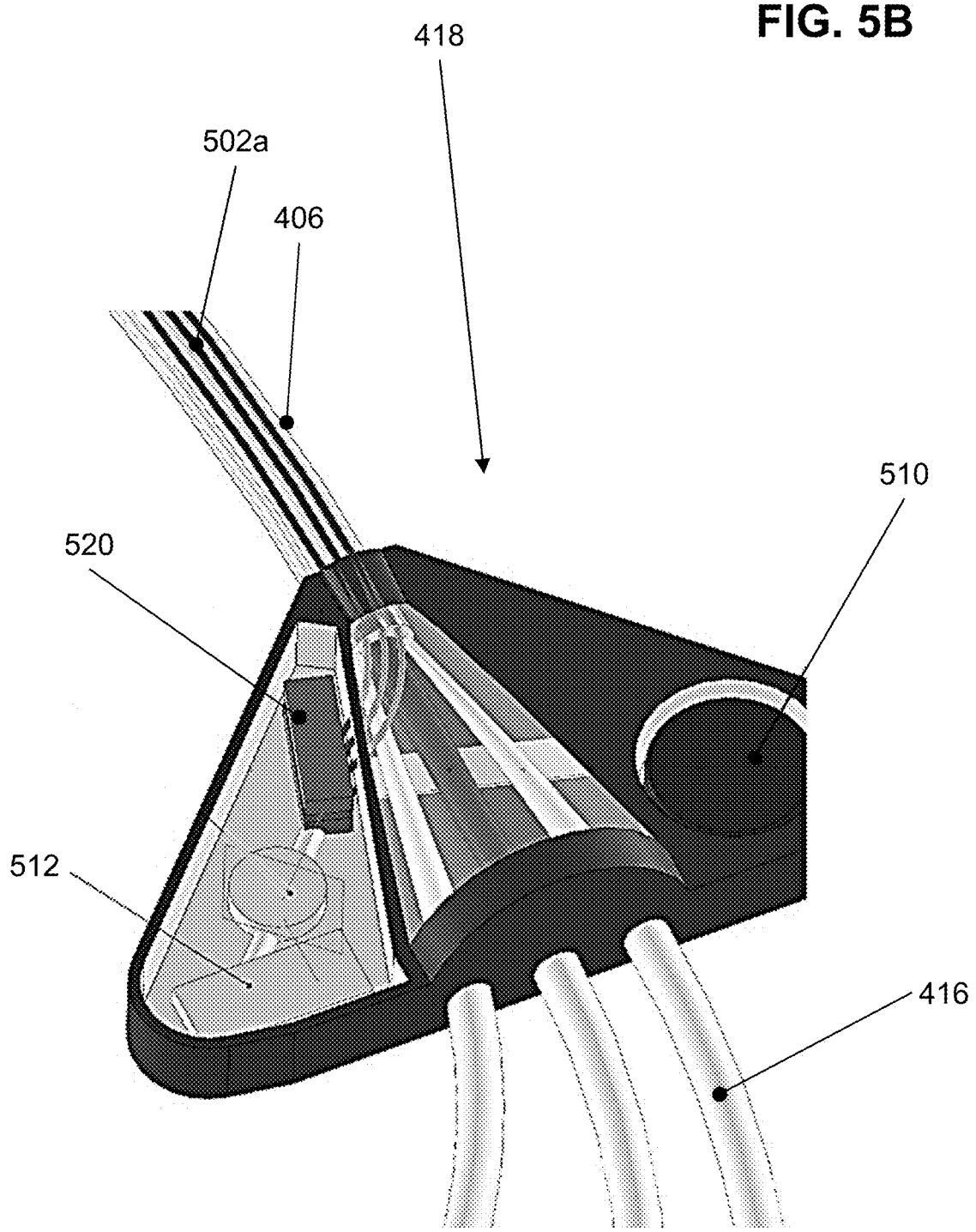
FIG. 5B is a close up cut away view of a system to prevent sorption in accordance with an embodiment of the current invention.

FIGS. 5A and 5B are close up views of section B of FIG. 4 showing a perspective view and a cutaway view respectively in accordance with an embodiment of the current invention. Optionally, a power source 510 (e.g. a battery) and/or a modulator (e.g. an A/C generator 512 and/or a processor 520) are located on an external portion of the catheter (for example on the bushing 418 and/or a suture wing of a catheter). Electrodes 502a, e.g. wires connected to the A/C generator 512, optionally pass along tube 406 of the catheter producing. For example, the wires are connected to the A/C generator 512 to produce an alternating electric field on an exposed surface of tube 406. For example, the field and/or system may be in accordance with the systems and/or methods of FIGS. 1 to 3.

In some embodiments, electrodes (e.g. 1 to 5 wires 502a on each side see FIG. 5A) are sealed inside the wall of tube 406. Optionally, the electrodes are not exposed to (e.g. are electrically insulated from) an inner and/or outer surface of the tube 406. Optionally, the electrodes are connected to a modulator (e.g. an oscillator 512 and/or a controller 520 which may include for example a printed circuit board PCB device). For example, the modulator may be connected to a power source 510 (e.g. a battery) and/or control the frequency, amplitude and/or voltage change in each electrode. Optionally voltages changes may be periodic and/or random. In some embodiments, the voltage changes will induce alternating electric field between oppositely charged wires 502a, 502b (e.g. see FIG. 6). The electric current between electrodes is optionally very small and/or negligible.

Figure 6:
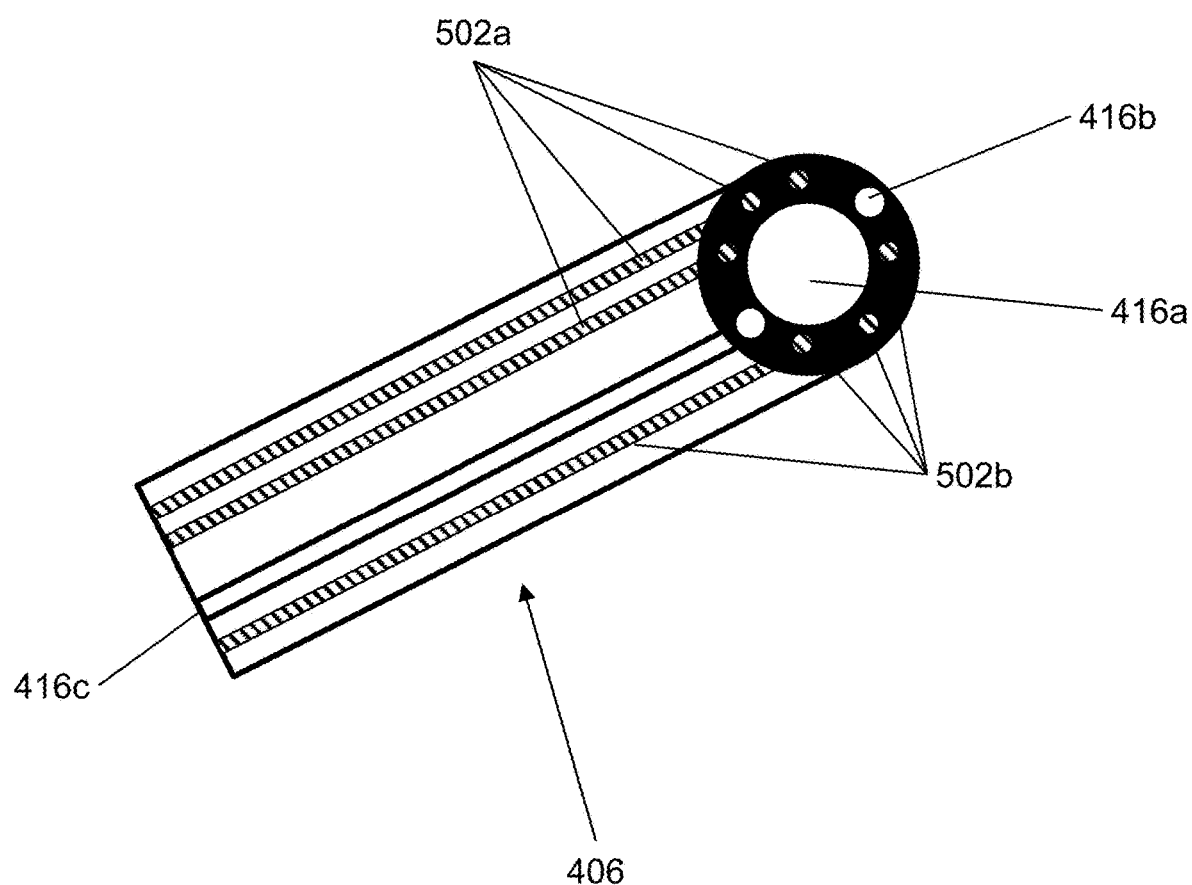
FIG. 6 illustrates a cross section of catheter tube in accordance with an embodiment of the current invention.

FIG. 6 illustrates a cross section of catheter tube 406 (for example a cross section across line D-D of FIG. 4) in accordance with an embodiment of the current invention. Optionally, wires 502a and 502b run along the length of the tube 406. Optionally wires 502a and 502b are charged with alternating current. For example, wires 502a on one side of the tube 406 have opposite polarity from wires 502b running along an opposite side of tube 406. For example, the tube 406 includes three medical lumens (a main lumen 416a and/or two secondary lumens 416b, 416c). Optionally, the electrodes (e.g. wires 502a, 502b are embedded in the walls of the catheter (e.g. inside a wall that has surfaces exposed to the biological medium).

Figure 7B:
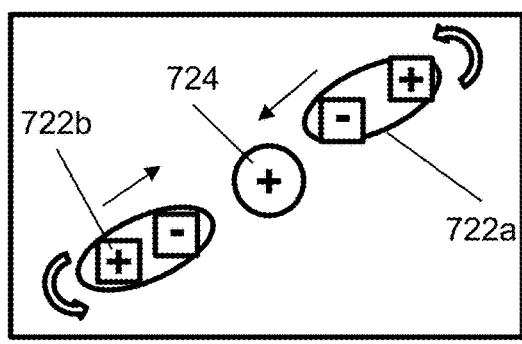
FIGS. 7A-7D is a schematic illustration of a possible conceptualization of inhibiting sorption in accordance with some embodiment of the current invention.
Figure 7A:
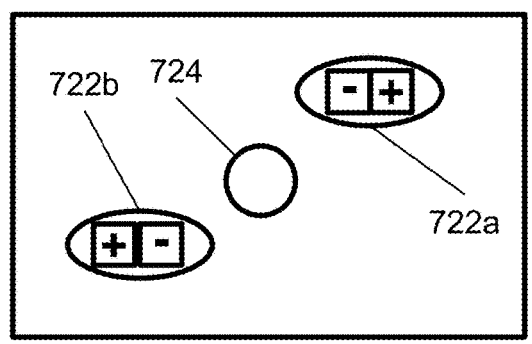
Figure 7D:
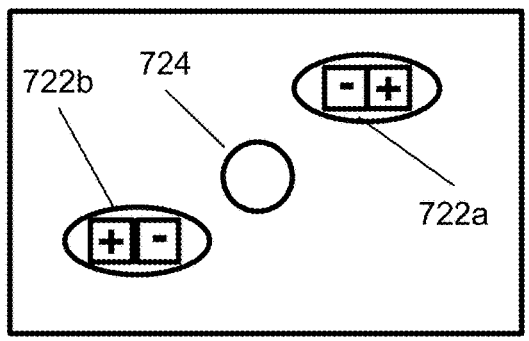
Figure 7C:
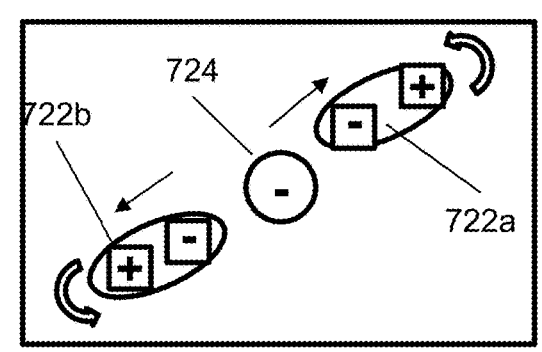

FIGS. 7A-7D is a schematic illustration of a possible conceptualization of inhibiting sorption in accordance with some embodiment of the current invention. For example, a fluid may include a surface 724 and/or polar molecules 722a, 722b as illustrated in FIG. 7A. Without limiting the invention to a theoretical conceptualization, in some embodiments, a process of adhesion between molecules (e.g. enzymes, proteins and/or a foreign body like an implant) may be facilitated by various types of electrical connections (e.g., a pole of a polarized molecule 722a, 722b may be oriented and/or attracted to a surface 724 of opposite charge for example as illustrated in FIG. 7B and/or a non-polarized molecule may become polarized and/or attracted to a charge for example by Van der Waals forces). In some embodiments, alternating voltage on a surface 724 (for example of a medical tube) may create a state of alternating rejections between the surface and the molecules 722a, 722b in a surrounding fluid (e.g. blood). In this way, the molecules 722a, 722b may approach the surface (e.g. as illustrated in FIG. 7B) and move away (e.g. as illustrated in FIG. 7C), but may be inhibited from establishing a stable connection with the surface and/or remain solution (e.g. as illustrated in FIG. 7D). Optionally, the rate of oscillation of the charge will be on the order of the time that it takes for a molecule 722a to rotate (for example between $1/10$ to 1 times the time and/or between 1 to 10 times the time and/or between 10 to 100 times the time and/or between 100 to 1000 times the time. For example, in a catheter this may inhibit a fouling process. Additionally or alternatively, alternating voltage may create an inverse electric field, which may cause rapid reversal in the direction of movement of the molecules towards each other, thus inhibiting bonding between them.

FIG. 7A depicts a schematic conceptualization of a situation where there is no charge at the surface 724 (for example an electrode near the surface 724 is not activated). Optionally, the molecules 722a, 722b are indifferent to it. For example, no charge may be induced during one stage in an alternating current pattern in accordance in some embodiments of the current invention.

FIG. 7B in another stage, the electrode and/or surface 724 may be loaded in a positive charge. The molecules 722a, 722b may rotate and/or stretch, so that a portion of the molecule with a negative charge is directed toward the positively charged electrode. A positively charged portion of the molecules 722a, 722b may move away from the electrode while the negative charge may approach the electrode. In some cases, attraction between the opposite charges is stronger than the repulsion of the identical charges for, example because the positive portion of the molecules 722a, 722b is further from the electrode than the negative portion. For example, molecules 722a, 722b may begin to move toward the electrode and/or surface 724.

FIG. 7C illustrates a conceptual view of reversal of the charge of an electrode. When the charge of the electrode is reversed (e.g. from positive to negative), a molecule 722a, 722b (for example the negative portion thereof that was directed toward the positive electrode) is repelled. Possibly later on, the molecule 722a, 722b will turn around and/or begin to be attracted to the electrode. This may result, in motion and/or rotation of the molecules 722a, 722b in a charge reversing region (for example according to the rate of polarization changes of the electrodes). Rotation of the molecules 722a, 722b themselves and/or extension and/or movement may inhibit sorption to a surface 724.

FIG. 7D illustrates returning to a non-charged state while sorption has been avoided.

Figure 8A:
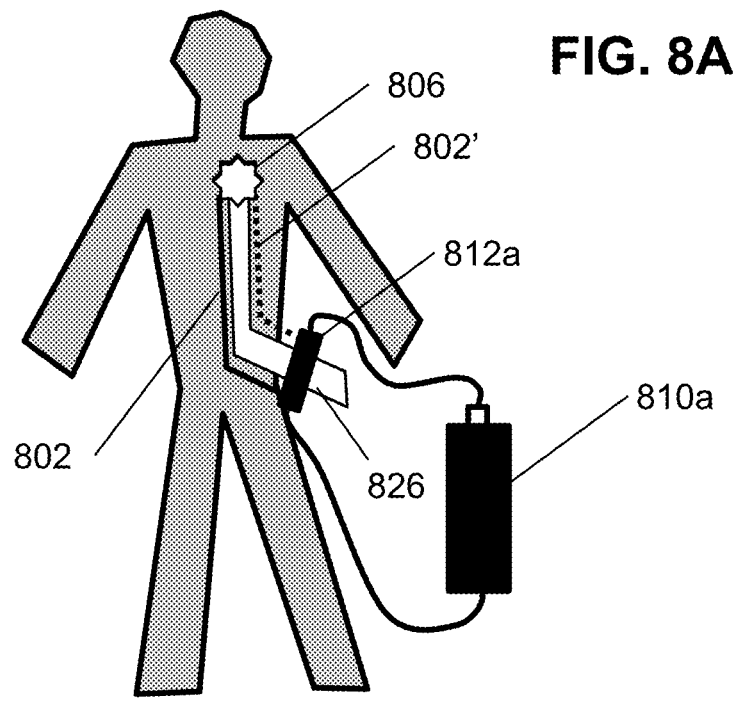
FIG. 8A illustrates an example of a catheter including an external electric field source in accordance with an embodiment of the current invention.

FIG. 8A illustrates an example of a catheter including an external electric field source (e.g. a power source 810a and/or a modulator 812a) in accordance with an embodiment of the current invention. For example, an electrode 802 carries an alternating charge and/or an opposing electrode 802' is loaded with an opposite charge. For example, the electrodes 802, 802' may include wires running along the length of a catheter 826. Optionally, in some embodiment, an electrode may be shaped to have a main effect at a particular location where blockage and/or fouling and/or film formation and/or sorption is expected to occur. For example, an electrode may be shaped to have a main effect near the end 806 and/or near an opening of a catheter. For example, the electrodes 802, 802' may twist around and/or have an increased surface area near the end 806 of the catheter 826.

Figure 8B:
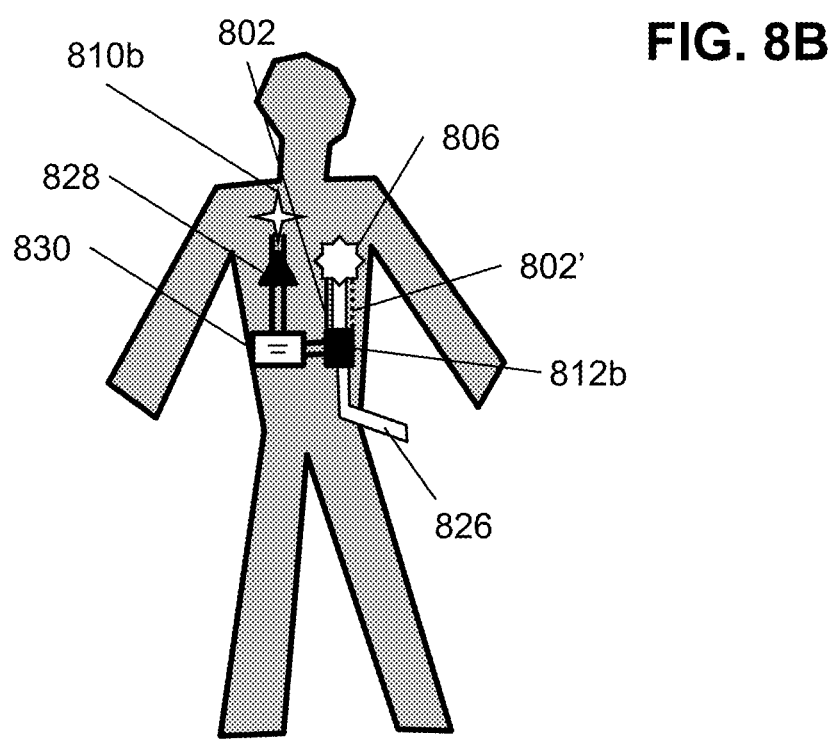
FIG. 8B illustrates an example of a catheter including an implanted electric field source in accordance with an embodiment of the current invention.

FIG. 8B illustrates an example of a catheter including an implanted electric field source in accordance with an embodiment of the current invention. Optionally, in some embodiment, an electrode 802, 802' may be shaped to have a main effect at a particular location where blockage and/or fouling and/or film formation and/or sorption is expected to occur. For example, an electrode may be shaped to have a main effect near the end 806 and/or near an opening of a catheter 826. Optionally a power source 810b may include a piezoelectric generator. For example, movement of the subject and/or of an inner body part may cause power to be generated. For example, the power may be rectified by a rectifier 828 and/or a capacitor 830 and/or modulated by a modulator 812b for example creating an electric field that inhibits blockage and/or fouling and/or film formation and/or sorption.

FIG. 9A to 9D illustrate various forms of sorption and/or fouling of a catheter that may be alleviated by some embodiments of the current invention. In some embodiments, blockage and/or sorption and/or fouling is expected to start on an outer surface and/or near an opening of a catheter. In accordance with some embodiment of the current invention one or more electrodes will be positioned near an opening of a catheter. For example, the electrode may be embedded into a wall of the catheter and/or insulated. Optionally the electrode may be located between 0.01 to 0.1 mm and/or between 0.1 to 1 mm and/or between 1 to 2 mm and/or between 2 to 5 mm and/or between 5 to 15 mm of a distal end of a catheter and/or an opening of a catheter.

Figure 9A:
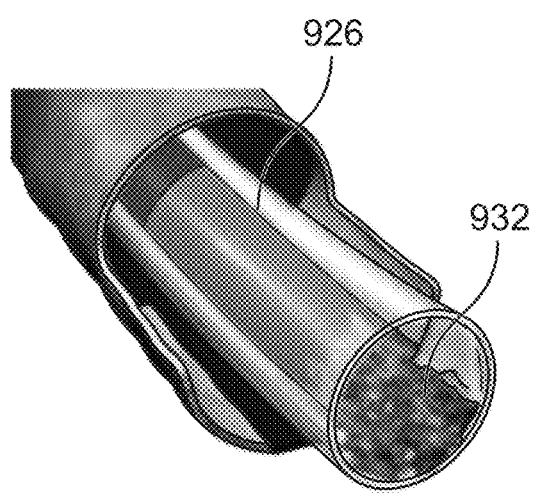
FIG. 9A illustrates a matrix of cells and debris that form a Fibrin Sheath.

FIG. 9A illustrates a matrix of cells and debris that form a Fibrin Sheath 932 around an end of a catheter 926. Such sheaths 932 are a known cause of central venous stenosis and catheter failure.

Figure 9B:
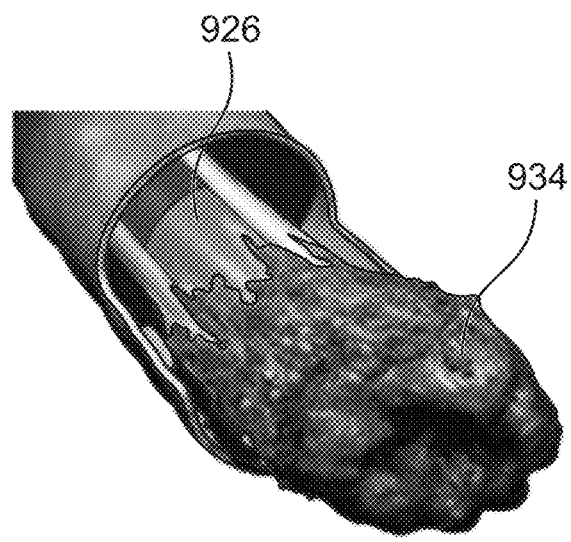
FIG. 9B illustrates an intraluminal catheter occlusion.

FIG. 9B illustrates an intraluminal catheter occlusion 934. For example, blood clot that adheres to the catheter wall and/or may occlude the tip of the catheter 926.

Figure 9C:
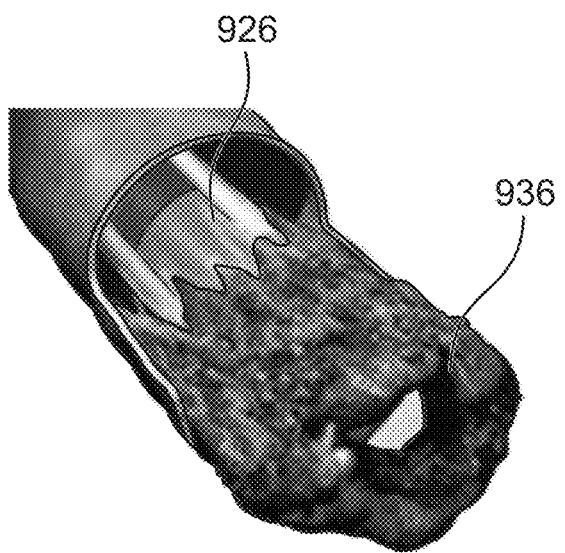
FIG. 9C illustrates a Fibrin tail.

FIG. 9C illustrates a Fibrin tail 936. For example, cells and/or debris may extend from the catheter tip and/or be drawn inward. The material may block the opening of the catheter 926 lumen.

Figure 9D:
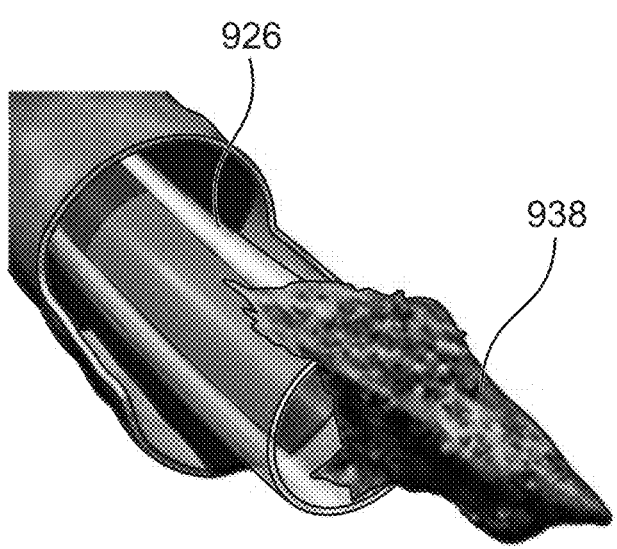
FIG. 9D illustrates a mural thrombus.

FIG. 9D illustrates a mural thrombus 938. For example, a thrombus 938 may form where the catheter 926 touches or "rubs" the wall of a natural lumen (for example a blood vein wall).

In some embodiments a system in accordance with the current invention (for example any of the embodiments described herein) may be used as a urinary catheter (for example the system may inhibit infection and/or forming biofilms and/or bacterial sorption to the catheter) and/or other catheters (e.g. pneumothorax, epidural, subarachnoid, brachial, subcutaneous, venous, umbilical, tunneled central, peripherally inserted central PICC) and/or implants for example implantable ports, stents, tube implants, shunts, drains, prosthetic valves.

FIG. 10A illustrates a piezoelectric device 1010 on the inside of an artery 1042 in accordance with an embodiment of the current invention FIG. 10B illustrate a piezoelectric device 1010 on the outside of an artery 1042 in accordance with an embodiment of the current invention. For example, a piezoelectric device 1010 may be triggered by pulsation of an artery 1042. For example, the device 1010 may inhibit blockage of an artery 1042. For example, a piezoelectric ring forming an alternating electric charge may be positioned around the artery 1042 and/or inside the artery (for example as part of stent). Optionally, the device may form an electric charge via a piezoelectric device, for example in response to pulsation of the artery as blood 1040 is pumped therethrough. Alternatively or additionally, the device may be connected to an external and/or internal power source (for example a battery and/or a modulator).

Various embodiments and aspects of the present invention as delineated hereinabove and as claimed in the claims section below find experimental support in the following examples.

Examples

Reference is now made to the following examples, which together with the above descriptions illustrate some embodiments of the invention in a non limiting fashion.

Figure 11:
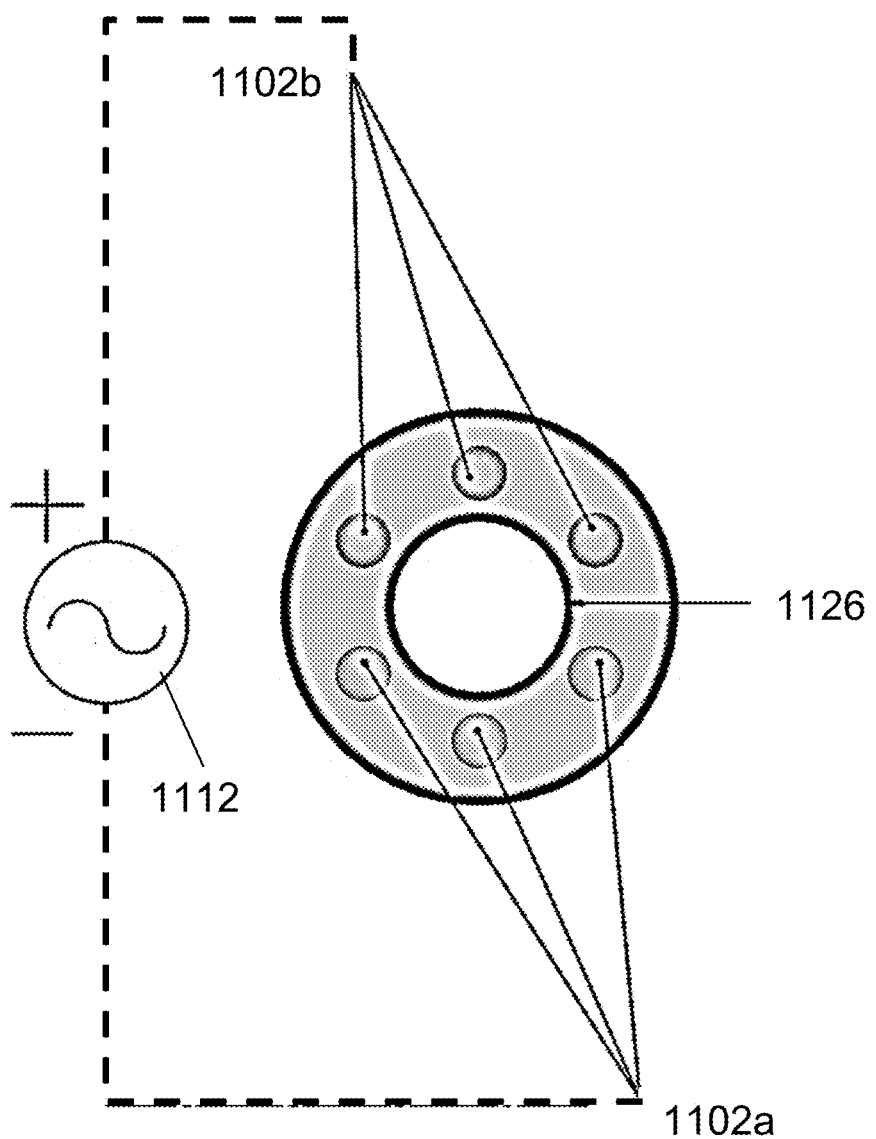
FIG. 11 is a schematic illustration of a catheter cross section as used in an exemplary experimental demonstration in accordance with an embodiment of the current invention.
Figure 12:
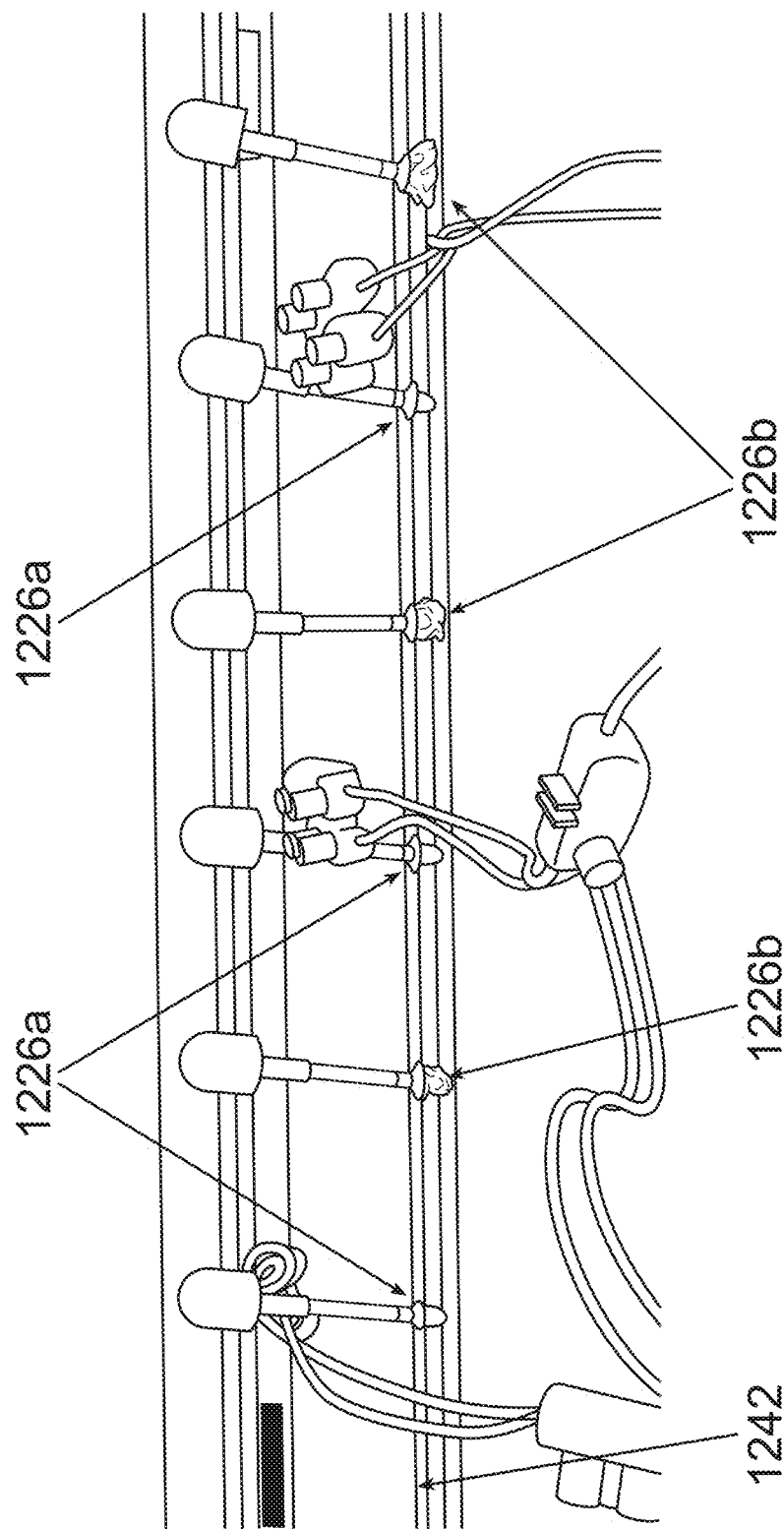
FIG. 12 is an image of an exemplary experimental demonstration in accordance with an embodiment of the current invention.

1. Nine catheters 1226a, 1226b (e.g. see FIG. 12) were printed within each catheter one central channel 1106 (e.g. see FIG. 11) passing through all of each catheter 1226a, 1226b and six additional electrode channels around the central channel in the wall thereof (FIG. 11)
2. The six extra electrode channels were open on a proximal end and had a closed "vein side" sealing the electrode channels, electrically insulating the electrode channels and preventing contact between fluid and tissue surrounding the catheter 1226a, 1226b and the electrodes.
3. Electrodes consisting of Metal wires 1102a and 1102b were inserted into the six electrode channels of these catheters.
4. In five test catheters of the nine catheters the electrodes were connected to an alternating voltage generator 1112. These are the active catheters. The other four catheters were used as a control.
5. The amplitude of the alternating voltage applied to the electrodes of the test catheters was 1V.
6. Three wires 1102a of each set were connected to '−' and the other wires 1102b three were connected to '+'. For example, three positive electrodes 1102b where grouped on one side of the catheter lumen while the remaining opposed charged electrodes 1102a (negative electrodes) were grouped on the opposite side of the lumen.
7. In different experiments, the voltage generator reversed the voltage between '+' and '−' at frequencies of 20, 200 and 2000 Hz.
8. All catheters were inserted into a larger tube 1242 with circulating fresh human blood using peristaltic pump.
9. The active and control catheters 1126a, 1126b were alternately arranged.
10. At the end of each experiment, flow of water through the catheters was measured comparing the active catheters 1126a to the control catheters 1126b.

In the exemplary tests, the most positive results in the test were seen at frequency of 200 Hz with four out of five experimental active catheters showing significantly higher flow compared to the control catheters. A photograph of the catheters at the end of the test (FIG. 12) shows the test catheters connected to blue wires and the controls without wires. Blood clots adsorbed to the opening of the control catheters is visible at the bottom of each control catheters. Fouling of the active catheters is visible less than the controls.

Figure 13:
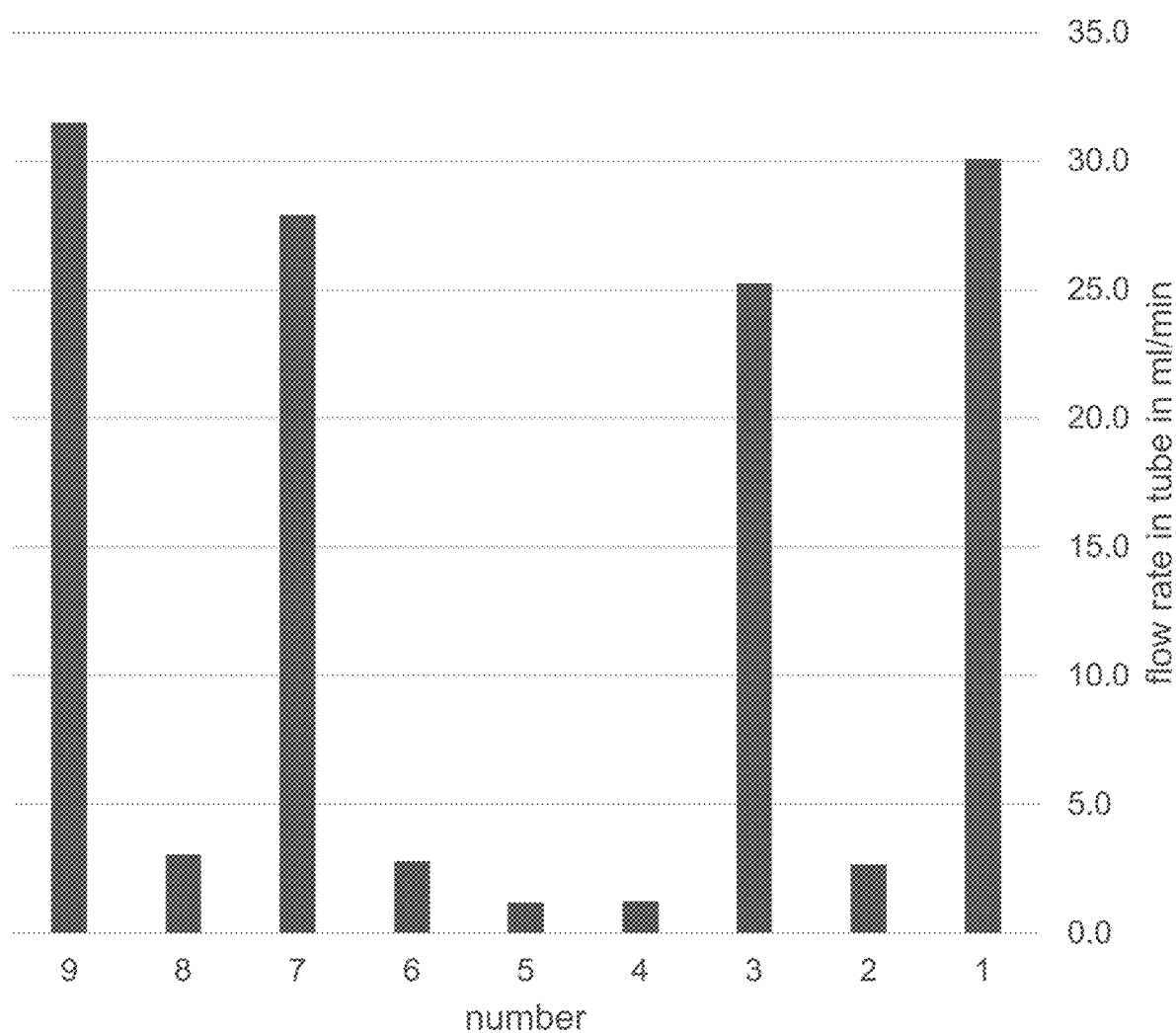
FIG. 13 is an image of an experimental results in accordance with an embodiment of the current invention.

The following Table 1 and FIG. 13 illustrate results after 43 hours of exposing the tubes to blood. The blood was cycled between 5 minutes still and 5 seconds pumping.

TABLE 1

Test Results

| flow rate ml/min | volume ml | electric signal | number |
|---|---|---|---|
| 30.1 | 18 | yes | 1 |
| 2.7 | 2 | no | 2 |
| 25.3 | 18 | yes | 3 |
| 1.3 | 1 | no | 4 |
| 1.2 | 1 | yes | 5 |
| 2.8 | 2 | no | 6 |
| 27.9 | 18 | yes | 7 |
| 3.1 | 2 | no | 8 |
| 31.5 | 18 | yes | 9 |

Four (catheters 1, 3, 7 and 9) out of the five (catheters 1, 3, 5, 7 and 9) test catheters 1226a showed significantly less sorption and significantly more flow than the control (2, 4, 6 and 8) catheters 1226b.

GENERAL

It is expected that during the life of a patent maturing from this application many relevant building technologies, artificial intelligence methodologies, computer user interfaces, image capture devices will be developed and the scope of the terms for design elements, analysis routines, user devices is intended to include all such new technologies a priori.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks might be expected to use completely different methods, e.g., making use of expert knowledge and/or the pattern recognition capabilities of the human brain, which would be vastly more efficient than manually going through the steps of the methods described herein.

As used herein the term "about" refers to ±20%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A catheter assembly comprising:
    a distal tube configured for insertion into a living subject, the distal tube including an inner surface and an outer surface;
    a lumen surrounded by said distal tube, and wherein the outer surface of said distal tube is in contact with said living subject and the inner surface of said distal tube is in contact with said lumen;
    a first electrode in said distal tube positioned to create an electric field in said lumen preventing sorption to at least one of said inner surface of said distal tube and said outer surface of said distal tube
    a power source;

a charge modulator in electrical communication between said first electrode and said power source for producing an alternating charge on said first electrode and thereby producing said electric field in said lumen;

electrical insulation electrically insulating said first electrode from said lumen, wherein said electrical insulation additionally electrically insulates said first electrode from any point on said inner surface of said distal tube, and wherein said electrical insulation additionally electrically insulates said first electrode from said outer surface of said distal tube, and wherein said electrical insulation additionally electrically insulates said first electrode from said living subject and wherein said first electrode is sealed from fluid communication with said lumen.

2. The catheter assembly of claim 1, wherein said power source, said charge modulator and said first electrode are configured to produce said alternating charge of frequency between 10 Hz to 20 kHz.

3. The catheter assembly of claim 1, wherein a shortest distance between said first electrode and said inner surface is less than 5 mm.

4. The catheter assembly of claim 1, wherein said first electrode is embedded inside a wall of said distal tube.

5. The catheter assembly of claim 4, wherein said electrical insulation and said wall of said distal tube are a single piece of insulating material.

6. The catheter assembly of claim 1, further comprising:
a second electrode connected to said charge modulator for carrying a charge opposite to said alternating charge on said first electrode and wherein said second electrode is electrically insulated from said lumen.

7. The catheter assembly of claim 6, wherein a shortest path connecting the first electrode to the second electrode passes across said electrical insulation and passes across a portion of said lumen.

8. The catheter assembly of claim 6, wherein said electrical insulation intervenes between said first and second electrodes such that there is negligible current between the first and second electrode.

9. The catheter assembly of claim 6, wherein said electrical insulation intervenes between said first and second electrodes such that there is no conductive path between the first electrode and the second electrode.

* * * * *